(12) United States Patent
Maruyama et al.

(10) Patent No.: US 9,383,495 B2
(45) Date of Patent: Jul. 5, 2016

(54) LATERAL LIGHT EMITTING DEVICE

(71) Applicant: TOYO SEIKAN GROUP HOLDINGS, LTD., Tokyo (JP)

(72) Inventors: Naofumi Maruyama, Kanagawa (JP); Toshiaki Fukuda, Kanagawa (JP)

(73) Assignee: Toyo Seikan Group Holdings, Ltd., Tokyo (JP)

( * ) Notice: Subject to any disclaimer, the term of this patent is extended or adjusted under 35 U.S.C. 154(b) by 0 days.

(21) Appl. No.: 14/771,723

(22) PCT Filed: Mar. 27, 2013

(86) PCT No.: PCT/JP2013/059100
§ 371 (c)(1),
(2) Date: Aug. 31, 2015

(87) PCT Pub. No.: WO2014/155584
PCT Pub. Date: Oct. 2, 2014

(65) Prior Publication Data
US 2016/0018581 A1 Jan. 21, 2016

(51) Int. Cl.
*F21V 8/00* (2006.01)
*G02B 6/26* (2006.01)
(Continued)

(52) U.S. Cl.
CPC ............ *G02B 6/0008* (2013.01); *A61B 1/0615* (2013.01); *A61B 1/07* (2013.01); *A61B 5/0066* (2013.01); *A61B 5/0084* (2013.01); *G02B 5/04* (2013.01); *G02B 6/262* (2013.01)

(58) Field of Classification Search
CPC ...... A61B 1/0615; A61B 1/07; A61B 5/0066; A61B 5/0084
USPC .................................. 362/146, 551
See application file for complete search history.

(56) References Cited

U.S. PATENT DOCUMENTS 6,263,133 B1 7/2001 Hamm
8,380,037 B2 * 2/2013 Maruyama ........... A61B 5/0066
385/146
(Continued)

FOREIGN PATENT DOCUMENTS

CN 1470894 1/2004
CN 101032388 9/2007
(Continued)

OTHER PUBLICATIONS

International Search Report issued Apr. 23, 2013 in International (PCT) Application No. PCT/JP2013/059100, with English translation.
(Continued)

*Primary Examiner* — Laura Tso
(74) *Attorney, Agent, or Firm* — Wenderoth, Lind & Ponack, L.L.P.

(57) ABSTRACT

To provide a lateral light emitting device that can prevent coupling efficiency in a fused portion of a rod lens and a prism from being deteriorated, can set an outside diameter extremely small, and set the distance to a beam waist long. A lateral light emitting device includes an optical fiber 2, a rod lens 3, one end of which is fused to the end surface of the optical fiber 3, and a prism 4 fused to the other end of the rod lens. The prism has a base shape obtained by cutting a part of the circumference of a cylinder and forming a flat emission surface 4c parallel to an axial line. In a fused portion of the rod lens and the prism, the outside diameter of a fused end surface of the rod lens is equal to or smaller than the smallest diameter of a fused end surface of the prism. The fused end surface of the rod lens does not protrude from the fused end surface of the prism. A center O1 of the fused end surface of the rod lens and a center O2 of a circular arc of the fused end surface of the prism are offset.

8 Claims, 9 Drawing Sheets

(51) Int. Cl.
*A61B 1/06* (2006.01)
*A61B 1/07* (2006.01)
*A61B 5/00* (2006.01)
*G02B 5/04* (2006.01)

(56) References Cited

U.S. PATENT DOCUMENTS

| | | | | |
|---|---|---|---|---|
| 2009/0262361 | A1* | 10/2009 | Tanioka | A61B 5/0066 356/479 |
| 2011/0316029 | A1 | 12/2011 | Maruyama et al. | |
| 2012/0243251 | A1 | 9/2012 | Suzuki et al. | |

FOREIGN PATENT DOCUMENTS

| | | |
|---|---|---|
| CN | 102281811 | 12/2011 |
| CN | 102667559 | 9/2012 |
| EP | 2 412 298 | 2/2012 |
| EP | 2 515 150 | 10/2012 |
| JP | 6-35946 | 5/1994 |
| JP | 2002-540465 | 11/2002 |
| JP | 2005-115097 | 4/2005 |
| JP | 4659137 | 1/2011 |
| WO | 00/58766 | 10/2000 |
| WO | 2008/081653 | 7/2008 |
| WO | 2011/074051 | 6/2011 |
| WO | 2011/108087 | 9/2011 |

OTHER PUBLICATIONS

Notification of Preliminary Rejection issued Oct. 30, 2015 in corresponding Korean Application No. 10-2015-7024452 with English translation.
Search Report issued Feb. 23, 2016 in European Application No. 13879685.9.
Office Action issued Mar. 1, 2016 in European Application No. 13978685.9.
Notice of Reasons for Refusal issued Apr. 12, 2016 in Chinese Application No. 201380075085.3, with English translation.

* cited by examiner

Prior Art

Prior Art

Prior Art

Prior Art

Prior Art

LATERAL LIGHT EMITTING DEVICE

TECHNICAL FIELD

The present invention relates to a lateral light emitting device that emits light propagating in an optical fiber to a lateral direction forming an angle with respect to the optical axis of the optical fiber and, more particularly, to a lateral light emitting device suitably used as a light probe of OCT (Optical Coherence Tomography).

BACKGROUND ART

The OCT is a light coherence tomographic imaging method for inserting a light probe into an organ such as a blood vessel or an intestine of a patient, emitting low coherence light from the distal end of the light probe, and obtaining a precise tomographic image of the inside of a subject using light reflected in places inside the subject and returning to the light probe. A basic technique of the OCT is disclosed in Japanese Examined Patent Publication No. H6-35946 (Patent Document 1). A specific configuration of the light probe is disclosed in WO2011/074051 (Patent Document 2), Japanese Patent No. 4659137 (Patent Document 3), and the like.

FIGS. 8 and 9 show a conventional lateral light emitting device 11 (light probe) described in Patent Document 2. In the lateral light emitting device 11, a rod lens 3 is fused to one end of an optical fiber 2 and a prism 41 having a square cross section is fused to the distal end surface of the rod lens 3. As shown in FIG. 9, the prism 41 is inscribed in the rod lens 3. Note that reference sign 2a denotes coating of the optical fiber.

The lateral light emitting device of Patent Document 2 has a characteristic that, since the prism 41 is inscribed in the rod lens 3, the outside diameter of the lateral light emitting device is extremely thin and the lateral light emitting device can be inserted into an extremely thin blood vessel or the like and used. The outside diameter of the lateral light emitting device is considered desirably 250 μm or less. However, when a rod lens having a diameter of 200 microns is used, the outside diameter of the lateral light emitting device is preferably 200 μm.

In the lateral light emitting device of this type, the distance from an emission surface to a beam waist (a focal length) is required to be set long to a certain degree. To set the distance long, it is advantageous to set a beam diameter in a fused portion of the rod lens 3 and the prism 41 large. However, there is a problem in that, as shown in FIG. 9, if the beam 5 protrudes to the outer side of the prism 41, coupling efficiency is deteriorated and the performance of the lateral light emitting device falls.

In a lateral light emitting device 12 shown in FIGS. 10 and 11, the rod lens 3 is fused to one end of the optical fiber 2, a prism 42 having a square cross section is fused to the distal end surface of the rod lens 3, and the prism 42 is circumscribed with the rod lens 3 (FIG. 11)

In this case, in a fused portion of the rod lens 3 and the prism 42, a beam does not protrude to the outer side of the prism 41. However, there is a problem in that the largest diameter of the prism 42 (i.e., the outside diameter of the lateral light emitting device) increases. For example, when an outside diameter d of the rod lens 3 is set to 200 μm, the largest diameter D of the prism 42 is 282 μm, which exceeds 250 μm and undesirable.

FIGS. 12 to 14 are a lateral light emitting device 13 in which a prism lens 43 is fused to one end of the optical fiber 2. In the prism lens 43, the distal end surface of a GRIN lens (Graded Index lens) having a circular cross section is set as an inclined surface 43a inclined with respect to an axial line and a rear end surface is set as a connection surface connected to the optical fiber. In the lateral light emitting device, the outside diameter can be set extremely small and coupling efficiency is satisfactory.

As shown in FIG. 14, in the lateral light emitting device 13, since an emission surface of a beam is a curved surface, when media around the emission surface are substances greatly different from a circumference portion such as the air and water, the shape of an emission beam is formed in an excessively crushed elliptical shape, i.e., the emission beams is a so-called line beam. The lateral light emitting device 13 has a problem in that a beam waist distance is extremely short.

FIGS. 15 and 16 show a conventional lateral light emitting device 14 described in Patent Document 3. The lateral light emitting device 14 includes the optical fiber 2, the rod lens 3, one end of which is fused to the end surface of the optical fiber 2, and a prism 44 fused to the other end of the rod lens 3. The prism 44 has a base shape obtained by cutting a part of the circumference of a cylinder and forming a flat emission surface 44c parallel to an axial line. The prism 44 has a distal end inclined surface 44a formed by obliquely cutting the distal end part of the prism 44. Light entered in the prism from the optical fiber 2 is reflected on the distal end inclined surface 44a and emitted from the emission surface 44c. The rod lens 3 and the prism 44 are fused such that a center O1 of the rod lens 3 and a center O2 of a circular arc of the prism 44 coincide with each other.

In the lateral light emitting device 14, since the emission surface 44a is flat, a beam shape is substantially circular. The distance to the beam waist can be set long compared with the distance shown in FIGS. 15 and 16.

In FIGS. 15 and 16, the outside diameter of the rod lens 3 and the largest diameter of the prism 44 (the diameter of the circular arc) are equal. In this case, the outside diameter of the lateral light emitting device can be set extremely small. However, there is a problem in that, as shown in FIG. 16, the beam 5 protrudes to the outer side of the prism 44 in a fused portion of the rod lens 3 and the prism 44, coupling efficiency is deteriorated, and the performance of the lateral light emitting device falls.

To prevent the beam 5 from protruding to the outer side of the prism 44, as shown in FIG. 17, the outside diameter d of the rod lens has to be set considerably larger than the largest diameter D of the prism 44. For example, when the outside diameter d of the rod lens is set to 200 μm and width W of the emission surface 44c is set to 200 μm, the largest diameter D of the prism 44 is 282 μm, which exceeds 250 μm and undesirable.

Note that, in this case as well, the center O1 of the rod lens and the circular arc center O2 of the prism 44 coincide with each other.

RELATED ART LITERATURE

Patent Literature

Patent Document 1: Japanese Examined Patent Publication No. H6-35946
Patent Document 2: WO2011/074051
Patent Document 3: Japanese Patent No. 4659137

SUMMARY OF THE INVENTION

Technical Problem

It is an object of the present invention to provide a lateral light emitting device that can prevent coupling efficiency in a fused portion of a rod lens and the prism from being deteriorated when a beam protrudes from a prism, can set an outside diameter extremely small (specifically, 250 μm or less) and set the distance to a beam waist to be long (specifically, 3000 microns or more).

Solution to Problem

The present invention is a lateral light emitting device comprising: an optical fiber, a rod lens, one end of which is fused to an end surface of the optical fiber; and a prism fused to the other end of the rod lens, the prism having a base shape obtained by cutting a part of a circumference of a cylinder and forming a flat emission surface parallel to an axial line, the prism having a distal end inclined surface obtained by obliquely cutting a distal end part of the prism, and light entered in the prism from the optical fiber being reflected on the distal end inclined surface and emitted from the emission surface, wherein
in a fused portion of the rod lens and the prism, an outside diameter of a fused end surface of the rod lens is equal to or smaller than the smallest diameter of a fused end surface of the prism, the fused end surface of the rod lens does not protrude from the fused end surface of the prism, and
a center of the fused end surface of the rod lens and a center of a circular arc of the fused end surface of the prism are offset.

Since the optical fiber and the rod lens are joined by fusing and the rod lens and the prism are joined by fusing, an adhesive layer is absent in an optical path and fluctuation in beam quality, deterioration in the beam quality due to peeling, and a come-off of the prism do not occur. Further, the lateral light emitting device can be easily manufactured using a conventional well-known fiber fusion device.

Since the fused end surface of the rod lens does not protrude to the outer side from the fused end surface of the prism, it is unlikely that the beam protrudes to the outer side of the prism in the fused portion of the rod lens and the prism, coupling efficiency is deteriorated, and the performance of the lateral light emitting device falls.

Since the center of the fused end surface of the rod lens and the circular arc center of the fused end surface of the prism are offset, it is possible to reduce the largest diameter of the prism and make the most of the prism cross section as a path through which light can pass. The decrease in the largest diameter of the prism means a decrease in the outside diameter of the lateral light emitting device.

The optical fiber is a single mode fiber in most cases. However, the optical fiber may be a polarization maintaining fiber, a multi-mode fiber, and a handle fiber for image transmission.

The rod lens needs to be quartz-based glass in order to be fused. A so-called GI type fiber, a core of which has a refractive index distribution, and a so-called GRIN lens, the entire cross section of which has a refractive index distribution, can be used.

As the rod lens, a lens obtained by fusion-bonding two kinds (or three or more kinds) of GRIN lens having different numerical apertures described in Japanese Patent Application Laid-Open No. 2005-115097 can also be used.

The prism needs to be quartz-based glass in order to be fused. The prism has a base shape (a so-called hog-backed shape) obtained by cutting a part of the circumference of a cylinder and forming a flat emission surface parallel to an axial line. Therefore, the prism can be easily manufactured by extending a polished base material (a base material obtained by polishing a part of the circumference of a cylindrical base material to be flat) having a sectional shape similar to the base shape (by forming the polished base material as a fiber). Further, the prism can be easily fused to the rod lens in a state of an elongated fiber.

An inclination angle ($\theta$ in FIG. 3) of the distal end inclined surface of the prism with respect to the emission surface is usually 45°. In that case, light is emitted in the lateral direction at an angle of 90° with respect to the axial line. By changing the inclination angle ($\theta$) of the distal end inclined surface, it is possible to change the emission angle of the light (FIG. 1). Coating such as mirror coat (Au coat, etc) and half mirror coat (dielectric multilayer film coat, etc.) can be applied to the distal end inclined surface according to necessity.

To manufacture the prism lens of the present invention, first, a cylindrical lens base material made of quartz-based glass is manufactured. The lens base material can be manufactured by a well-known method (e.g., Japanese Patent Application Laid-Open No. 2005-115097). Subsequently, a part of the circumference of the lens base material is polished to form a polished base material having a flat polished surface parallel to the axial line. The polishing can also be easily performed using a normal polishing device. Subsequently, the polished lens base material is extended to form a fiber for a prism lens. The extension of the polished lens base material can be performed using a device that extends the optical fiber and the GRIN lens.

The present invention is the lateral light emitting device, wherein the outside diameter of the fused end surface of the rod lens is equal to the smallest diameter of the fused end surface of the prism.

The smallest diameter of the prism is D-L in FIG. 4. Note that D represents the largest diameter (the diameter of the cylinder before cutting) and L represents a cut amount. By setting the outside diameter of the fused end surface of the rod lens equal to the smallest diameter of the fused end surface of the prism (FIG. 4), it is possible to make the most of the prism cross section as a path through which light passes.

The present invention is the lateral light emitting device, wherein the largest diameter of the prism is twice or less as large as an optical fiber diameter.

When the largest diameter of the prism is twice or less as large as the optical fiber diameter, the outside diameters of the optical fiber and the rod lens are approximate to each other. The axes of the rod lens and the optical fiber automatically coincide with each other according to a self-alignment effect due to surface tension in fusing. Therefore, a joining loss of the optical fiber and the rod lens is extremely small. When the outside diameter of the optical fiber is 125 μm, 124 μm to 200 μm are appropriate as the outside diameter of the rod lens. 250 μm or less is appropriate as the largest diameter of the prism.

The present invention is the lateral light emitting device, wherein a most distal end part of the prism is chamfered in a chamfering process.

Since the most distal end part of the prism is chamfered, when the lateral light emitting device is directly inserted into a subject without being covered with a sheath, the subject is less easily scratched.

As the chamfering, for example, there is a method of smoothing the most distal end part of the prism in a curved surface shape through an electric discharge process, a laser process, or the like.

Advantageous Effects of the Invention

In the lateral light emitting device of the present invention, the fused end surface of the rod lens does not protrude to the outer side from the fused end surface of the prism. Therefore, it is unlikely that the beam protrudes to the outer side of the prism in the fused portion of the rod lens and the prism, coupling efficiency is deteriorated, and the performance of the lateral light emitting device falls.

The center of the fused end surface of the rod lens and the circular arc center of the fused end surface of the prism are offset. Therefore, it is possible to reduce the largest diameter of the prism, that is, the outside diameter of the lateral light emitting device and make the most of the prism cross section as a path through which light can pass.

In the lateral light emitting device of the present invention, an adhesive is not used. Therefore, fluctuation in beam quality due to an adhesive layer does not occur.

The optical fiber and the rod lens are integrally joined by fusing and the rod lens and the prism are integrally joined by fusing. Therefore, it is unlikely that bonding of a joined portion peels and beam quality is deteriorated. It is also unlikely that the prism and the rod lens come off and remain in a subject. It is unnecessary to cover the prism and the rod lens with a sheath.

DESCRIPTION OF EMBODIMENTS

Figure 1:
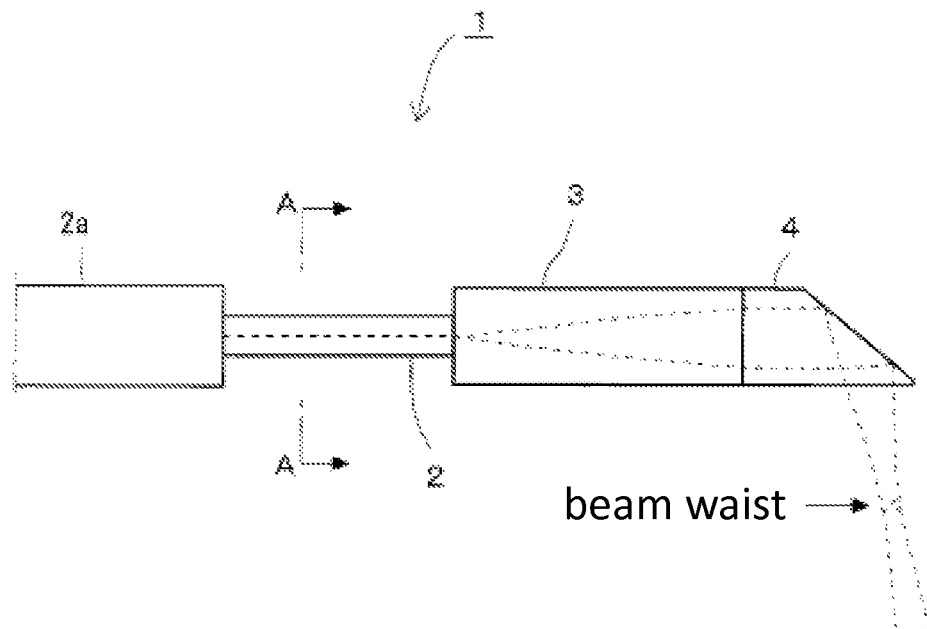
FIG. 1 is a side view of a lateral light emitting device 1 in an embodiment.
Figure 2:
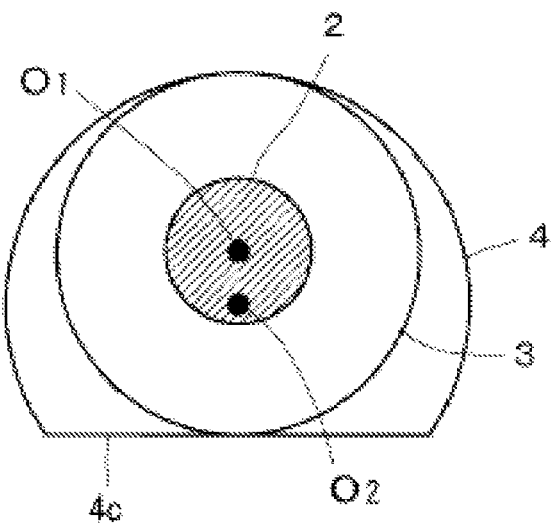
FIG. 2 is an A-A line sectional view in FIG. 1.
Figure 3:
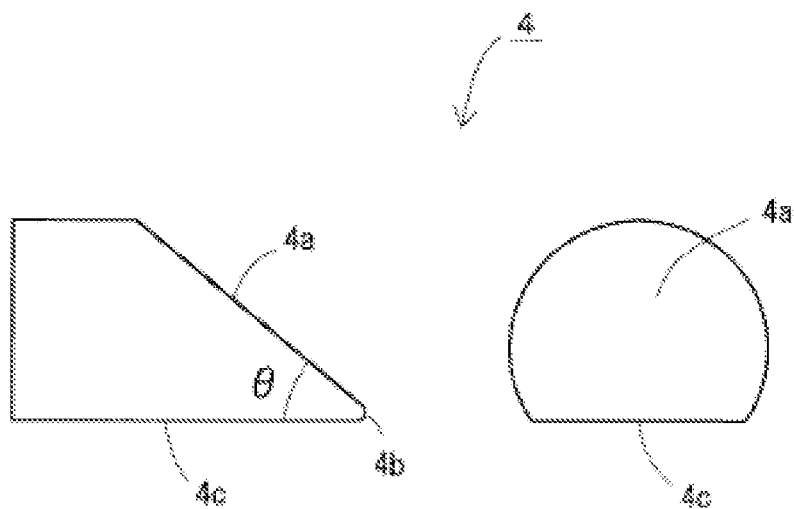
FIG. 3 is a side view (the left side) and a front view (the right side) of a prism 4.

FIGS. 1 to 3 relates to a lateral light emitting device 1 in an embodiment of the present invention. FIG. 1 is a side view,
FIG. 2 is an A-A line sectional view of FIG. 1, and FIG. 3 is a side view (the left side) and a front view (the right side) of a prism 4.

The lateral light emitting device 1 includes an optical fiber 2, a rod lens 3, and a prism 4.

The optical fiber 2 is a single mode optical fiber having an outside diameter of 125 μm. Coating 2a at the distal end part is removed. The rod lens 3 is fused to the distal end surface of the optical fiber 2.

The rod lens 3 is a GRIN lens made of quartz-based glass and having an outside diameter of 200 μm and a numerical aperture NA=1.53. The axes of the optical fiber 2 and the rod lens 3 automatically coincide with each other according to self-alignment effect in fusing.

Figure 4:
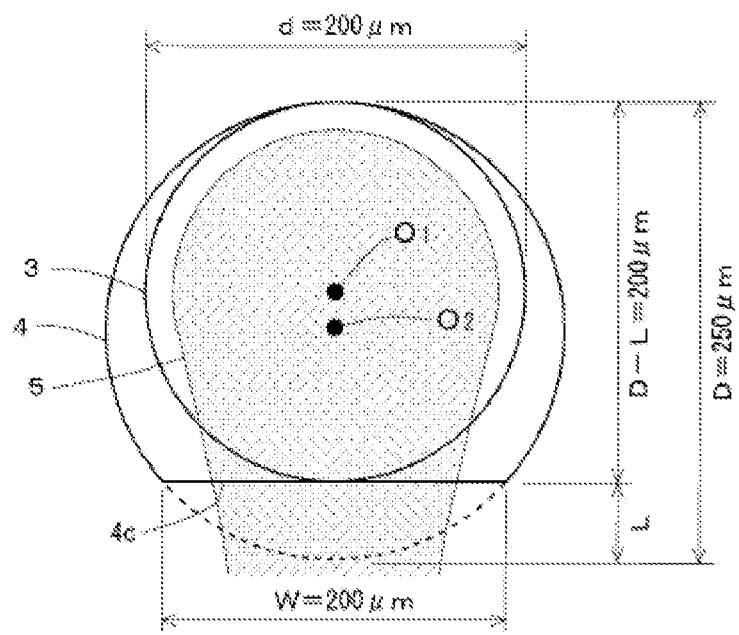
FIG. 4 is an explanatory diagram of a positional relation between a rod lens 3 and the prism 4 in a fused portion.

The prism 4 is quartz glass and has a base shape obtained by cutting, by 50 μm, a part of the circumference of a cylinder having a diameter of 250 μm, leaving the cylinder to have the smallest diameter of 200 μm, and forming a flat emission surface 4c (the width of an emission surface is 200 μm) parallel to an axial line. (FIG. 4)

The prism 4 is obtained by polishing a part of the circumference of a base material of a cylindrical quartz glass having a diameter of approximately 5 to 7 mm to be a sectional shape shown on the right side of FIG. 3 to form a polished base material, cutting a fiber for a prism obtained by extending the polished base material at temperature of approximately 1900° C., obliquely polishing the fiber at an inclination angle θ to form a distal end inclined surface 4a, thereafter applying chamfering to the most distal end part 4b through discharge machining, and further applying Au coat to the distal end inclined surface 4a.

A polished surface of the polished base material is a plane parallel to the axis of the base material.

Temperature in extending the optical fiber is usually 2000° C. However, when the fiber for the prism is extended, it is desirable to perform the extension at a lower temperature, which is approximately 1900° C. If the extension temperature is high, it is likely that an emission surface 4c of the extended fiber for the prism is rounded. When the extension temperature is set to approximately 1900° C., a curvature of the emission surface 4c is extremely small. The emission surface 4c is substantially a plane and no practical problem occurs.

As a result of measuring a beam waist distance and a beam waist diameter of an emission beam in water of the lateral light emitting device 1, the beam waist distance was 4665 μm and the beam waist diameter was 83.2 μm, which were satisfactory results.

A positional relation between the rod lens 3 and the prism 4 in a fused portion of the lateral light emitting device 1 is as shown in FIG. 4.

An outside diameter d of the rod lens 3 is 200 μm. The largest diameter D of the prism 4 is 250 μm. The prism 4 is cut with a cut amount L of 50 μm to set the smallest diameter D-L to 200 μm. Width W of the emission surface 4c is 200 μm Therefore, the outside diameter d of a fused end surface of the rod lens 3 is equal to the smallest diameter D-L of a fused end surface of the prism 4. A center O1 of the rod lens 3 and a circular arc center (the center of a circle before cutting) O2 of the prism 4 are offset by 25 μm. The rod lens 3 is inscribed in the prism 4.

Figure 17:
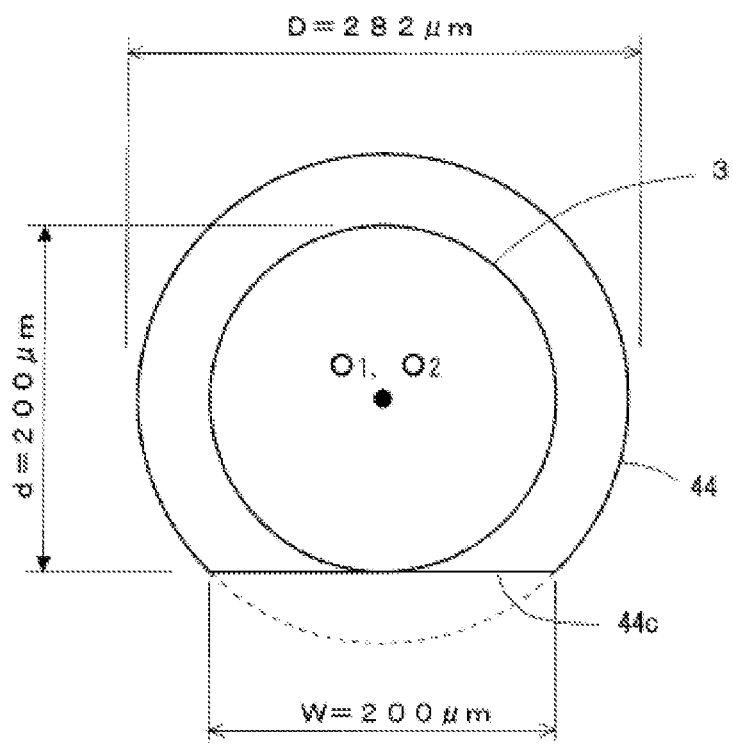
FIG. 17 is an explanatory diagram of a positional relation between the rod lens 3 and the prism 44 in a conventional lateral light emitting device (a comparative example).

FIG. 17 is a comparative example in which the center O1 of the rod lens 3 and the circular arc center O2 of the prism 4 overlap without being offset. The diameter d of the rod lens 3 is 200 μm and the width W of the emission surface 44c is 200 μm, both of which are the same as those in the embodiment shown in FIG. 4. However, the largest diameter D of the prism 4 is 282 μm, which is 32 μm larger than D=250 μm in the embodiment and is undesirable.

Figure 5:
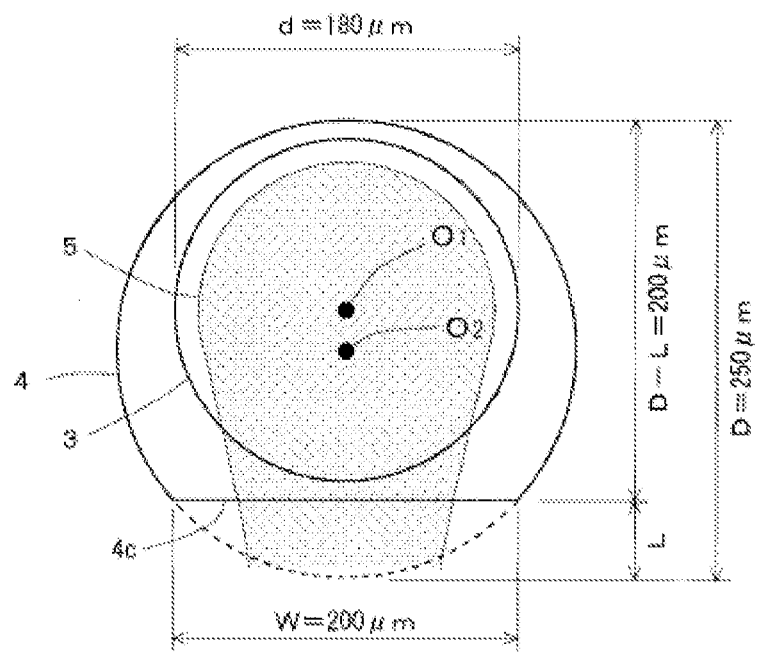
FIG. 5 is an explanatory diagram of a positional relation between the rod lens 3 and the prism 4 in the fused portion.

In the lateral light emitting device shown in FIG. 4, when a beam diameter in the emission surface 4c was measured, the beam diameter was 142 μm in the case of a numerical aperture NA=1.53 of a rod lens. When a rod lens with a numerical aperture NA=1.61 was used, the beam diameter was 135 μm FIG. 5 shows a positional relation between the rod lens 3 and the prism 4 in the fused portion in the case in which the prism 4 was completely the same as the prism 4 shown in FIG. 4 and a rod lens with the outside diameter d=180 μm was used. In this case, the center O1 of the rod lens 3 and the circular arc center (the center of the circle before cutting) O2 of the prism 4 are offset by 25 μm. The rod lens 3 does not project from the prism 4 and fits on the inner side.

Figure 6:
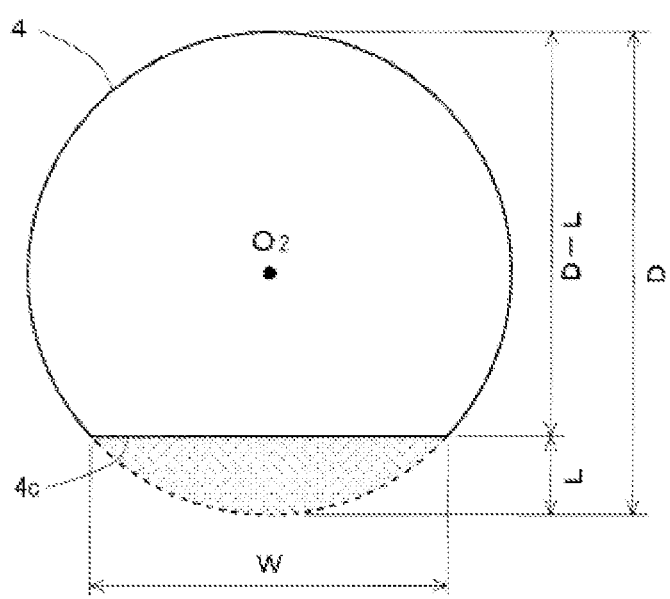
FIG. 6 is an explanatory diagram of the sectional shape of the prism 4.

In the lateral light emitting device shown in FIG. 5, as a result of measuring a beam diameter on the emission surface 4c, the beam diameter was 129 μm when the numerical aperture NA of a rod lens was 1.53. When a rod lens with the numerical apertures NA=1.61 was used, the beam diameter was 122 μm FIG. 6 is an explanatory diagram of a sectional shape of the prism 4. A base shape of the prism 4 is a circular shape having a diameter D. A part of the circumference of the prism 4 is cut in a bow shape having thickness L to form the flat emission surface 4c having width W.

Figure 7:
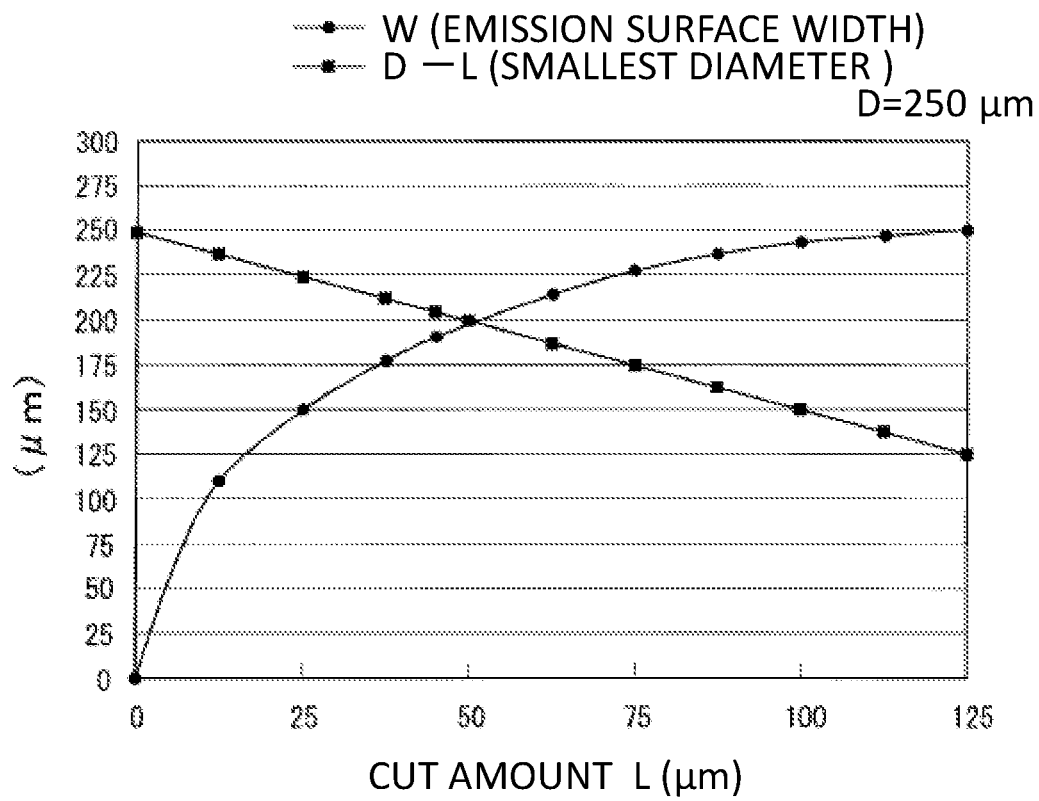
FIG. 7 is an explanatory diagram of a relation among a cut amount L, an emission surface width W, and the smallest diameter D-L.
Figure 8:
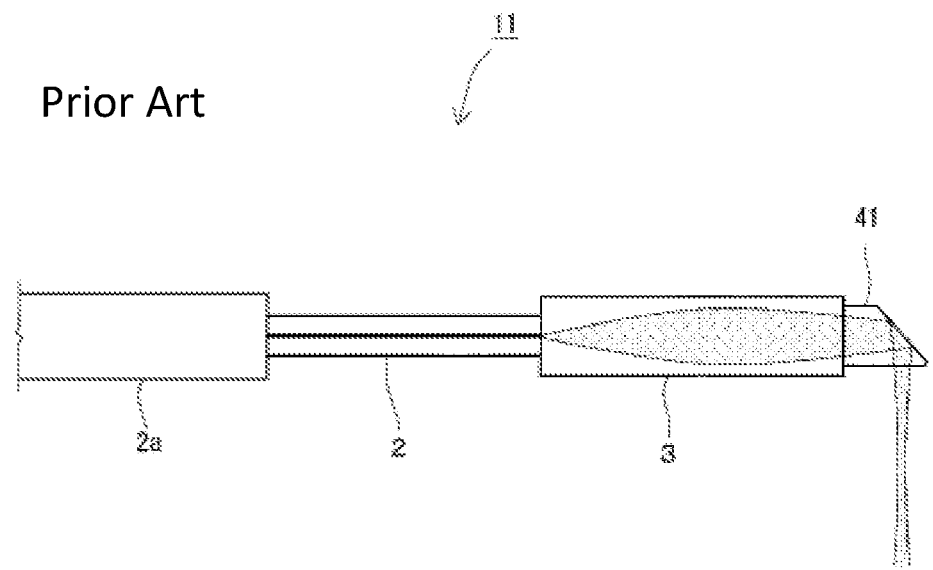
FIG. 8 is a side view of a conventional lateral light emitting device 11.
Figure 9:
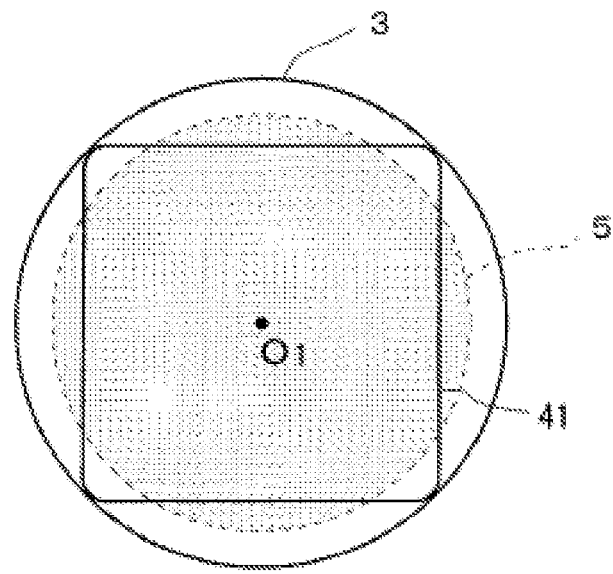
FIG. 9 is an explanatory diagram of a positional relation between the rod lens 3 and a prism 41 in a fused portion of the lateral light emitting device 11.
Figure 10:
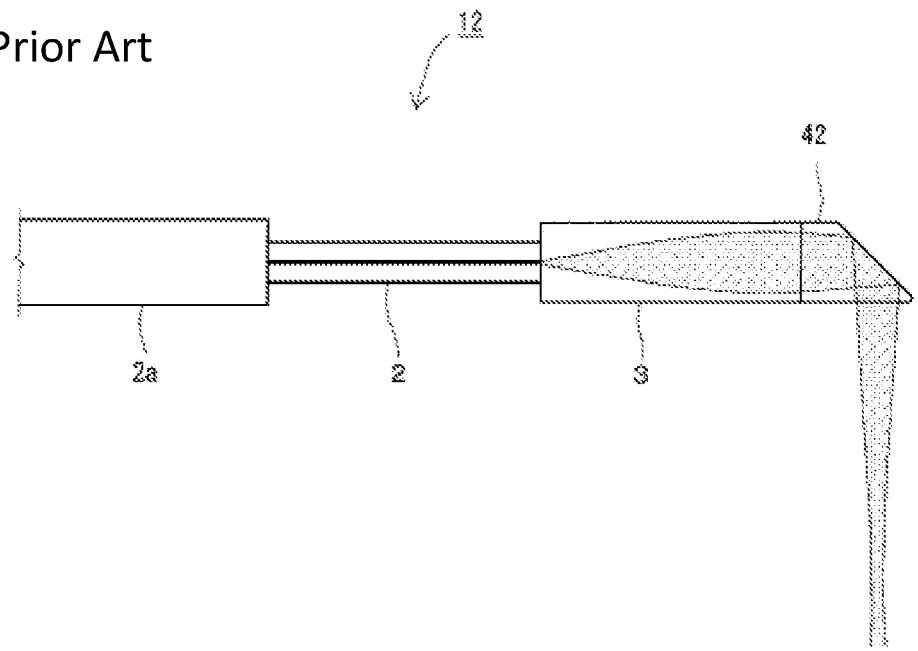
FIG. 10 is a side view of a conventional lateral light emitting device 12.
Figure 11:
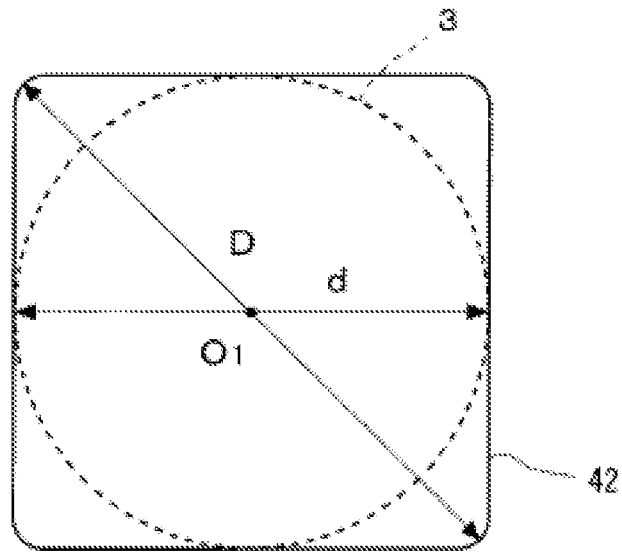
FIG. 11 is an explanatory diagram of a positional relation between the rod lens 3 and a prism 42 in a fused portion of the lateral light emitting device 12.
Figure 12:
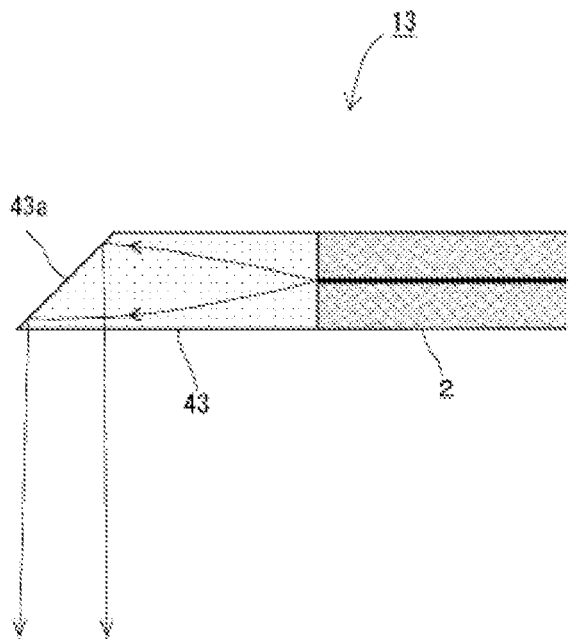
FIG. 12 is a side view of a conventional lateral light emitting device 13.
Figure 13:
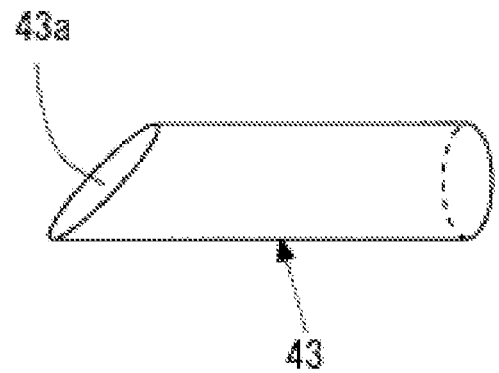
FIG. 13 is an explanatory diagram of a prism lens 43.
Figure 14:
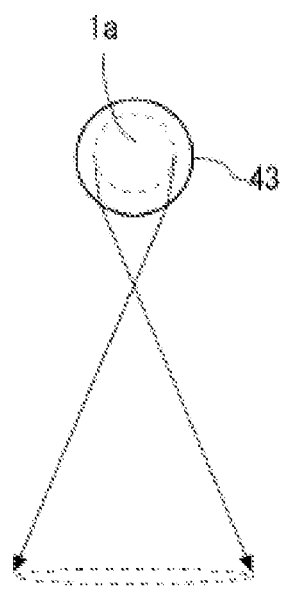
FIG. 14 is an explanatory diagram of an emission beam of the lateral light emitting device 13.
Figure 15:
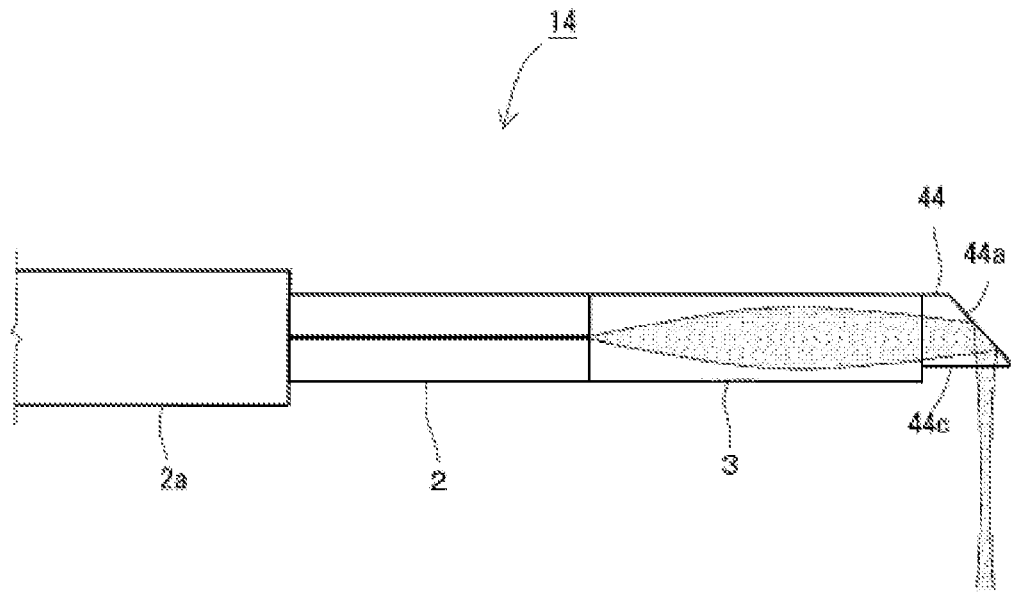
FIG. 15 is a side view of a conventional lateral light emitting device 14.
Figure 16:
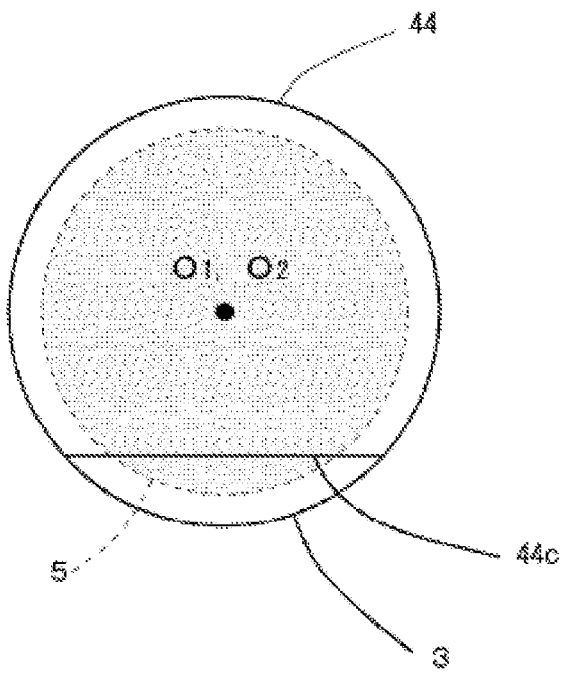
FIG. 16 is an explanatory diagram of a positional relation between the rod lens 3 and a prism 44 in a fused portion of the lateral light emitting device 14.

FIG. 7 shows a relation among the cut amount L, the emission surface width W, and the smallest diameter D-L in the case of D=250 μm For example, in the case of the cut amount L=50 μm, the emission surface width W is 200 μm and the smallest diameter D-L is 200 μm

INDUSTRIAL APPLICABILITY

The lateral light emitting device of the present invention is used as a light probe of the OCT. Besides, the lateral light emitting device can be used as an optical fiber module for optical communication such as joining of a laser diode and a single mode fiber, a light probe for a distance/displacement sensor, a light probe for an endoscope, and the like.

1 Lateral light emitting device
1a Wave guide
11 Lateral light emitting device
12 Lateral light emitting device
13 Lateral light emitting device
14 Lateral light emitting device
2 Optical fiber
2a Coating
3 Rod lens
4 Prism
4a Distal end inclined surface
4b Most distal end part
4c Emission surface
41 Prism
42 Prism
43 Prism lens
44 Prism
5 Beam

What is claimed is:

1. A lateral light emitting device comprising: an optical fiber; a rod lens, one end of which is fused to an end surface of the optical fiber; and a prism fused to the other end of the rod lens, the prism having a base shape obtained by cutting a part of a circumference of a cylinder and forming a flat emission surface parallel to an axial line, the prism having a distal end inclined surface obtained by obliquely cutting a distal end part of the prism, and light entered in the prism from the optical fiber being reflected on the distal end inclined surface and emitted from said emission surface, wherein in a fused portion of said rod lens and the prism, an outside diameter of a fused end surface of the rod lens is equal to or smaller than the smallest diameter of a fused end surface of the prism, the fused end surface of the rod lens does not protrude from the fused end surface of the prism, and a center of the fused end surface of the rod lens and a center of a circular arc part of the fused end surface of the prism are offset.

2. The lateral light emitting device according to claim 1, wherein the outside diameter of the fused end surface of said rod lens is equal to the smallest diameter of the fused end surface of said prism.

3. The lateral light emitting device according to claim 1, wherein the largest diameter of said prism is twice or less as large as an optical fiber diameter.

4. The lateral light emitting device according to claim 1, wherein a most distal end part of said prism is chamfered in a chamfering process.

5. The lateral light emitting device according to claim 2, wherein the largest diameter of said prism is twice or less as large as an optical fiber diameter.

6. The lateral light emitting device according to claim 2, wherein a most distal end part of said prism is chamfered in a chamfering process.

7. The lateral light emitting device according to claim 3, wherein a most distal end part of said prism is chamfered in a chamfering process.

8. The lateral light emitting device according to claim 5, wherein a most distal end part of said prism is chamfered in a chamfering process.

* * * * *